United States Patent [19]
Syrenne

[11] 3,943,960
[45] Mar. 16, 1976

[54] CHEMICAL DISPENSER

[75] Inventor: Marius H. Syrenne, Saskatoon, Canada

[73] Assignee: National Sanitation Services, Ltd., Saskatoon, Canada

[22] Filed: Oct. 4, 1973

[21] Appl. No.: 403,424

[52] U.S. Cl. .................. 137/268; 239/310; 239/317
[51] Int. Cl.² .................. B01D 33/38; B01D 11/02; A01C 15/00
[58] Field of Search ............... 23/272.6 R; 137/268; 239/317, 310, 315

[56] References Cited
UNITED STATES PATENTS

| | | | |
|---|---|---|---|
| 811,749 | 2/1906 | Somers | 239/317 X |
| 2,228,922 | 1/1941 | Gorlick | 239/310 X |
| 3,052,525 | 9/1962 | Vogelmann et al. | 137/268 X |
| 3,195,985 | 7/1965 | Elkin | 239/317 X |

FOREIGN PATENTS OR APPLICATIONS

| | | | |
|---|---|---|---|
| 140,964 | 9/1930 | Switzerland | 239/317 |

*Primary Examiner*—Martin P. Schwadron
*Assistant Examiner*—Robert J. Miller

[57] ABSTRACT

Dispensers for chemicals usually have ball check valves and other moving parts which often corrode due to the action of the chemical. Other types may eliminate the moving parts, but have to be re-charged each time they are used. This device consists of a container having a water inlet and a water outlet at the under end. A U-shaped tube depends within the container and is secured to the inlet and outlet means is provided with a plurality of small holes to allow some of the water to enter a container. An outlet branch is secured within the container, to the outlet means and water is picked up from the container by the outlet branch and joins the mainstream of water passing through the U-shaped tube. Chemical in a fabric bag is placed in the container and dissolves in the water in the container and is picked by the outlet tube. When the water is shut off, the container may drain by siphoning action until the outlet branch is reached by the water level which breaks the siphon action so that some water always remains in the container covering the bag in order to dissolve the chemical contained therein.

2 Claims, 2 Drawing Figures

CHEMICAL DISPENSER

BACKGROUND OF THE INVENTION

This invention relates to means for disinfecting various facilities such as floors, stalls, walls of barns, dairy farm equipment, kitchen facilities and utensils, washroom facilities, urinals and the like.

Such devices are often used in series with the cleaning or flushing water under pressure.

One type uses a liquid within a container some of which is picked up as the water passes through or over the liquid much along the lines of a paint spraying device.

Other devices use slugs within the main stream of the water which dissolves slowly.

The principal disadvantage of the former type is the fact that a relatively fine tube is required in order to give the necessary pickup action and although this is satisfactory for use with a liquid chemical, it often becomes clog when is used with a powdered type chemical which has to dissolve in the water before it can be effective.

A disadvantage of the second type is the fact that the slugs are usually relatively small and no control is present for controlling the amount of chemical entering the water stream. Furthermore, when the water is shut off, the slug dries out and often crumbles so that considerable wastage occurs.

Other types of chemical dispenser use ball check valve and other moving parts, many of which may be attacked by the chemical action of the chemical used.

SUMMARY OF THE INVENTION

The present invention overcomes all of these advantages by providing a simple dispenser within which a powdered chemical may be placed in a porous bag or sac. The mainstream of water passes through a U-shaped tube in the container or dispenser which is provided with one or more small apertures so that some water passes into the container and fills same. This dissolves the chemical and the water now impregnated with the chemical is picked up by a water outlet branch adjacent the outlet to the container.

The principal object and essence of the invention is to provide a container or dispenser which can rapidly be attached to any water supply tap or hose so that the container will be flooded or filled with water when the tap is opened.

Another object of the invention is to provide a device of the character herewithin described in which the small quantity of water passing into the container creates a turbulence or stirring action to assist in dissolving the powdered chemical and in mixing same with water within the container.

Another object of the invention is to provide a device of the character herewithin described which is particularly suitable for use with a bacteria side to disinfect various facilities either by use of a spray nozzle on the outlet side of the dispenser or by incorporating the dispenser into a flushing system such as used with toilets and urinals.

Still another object of the invention is to provide a device of the character herewithin described in which the container does not empty completely when the water is shut off so that the powdered chemical always remains submerged thus generating a chemical solution ready for use when the tap is next turned on.

Still another object of the invention is to provide a device of the character herewithin described in which the powdered chemical is contained within a porous sac or bag within the base of the container or dispenser.

Another object of the invention is to provide a device of the character herewithin described which is simple in construction, economical in manufacture and otherwise well suited to the purpose for which it is designed.

With the foregoing objects in view, and other such objects and advantages as will become apparent to those skilled in the art to which this invention relates as this specification proceeds, my invention consists essentially in the arrangement and construction of parts all as hereinafter more particularly described, reference being had to the accompanying drawings in which:

BRIEF DESCRIPTION OF THE DRAWINGS

In the drawings like characters of reference indicate corresponding parts in the different figures.

DETAILED DESCRIPTION

Figure 1:
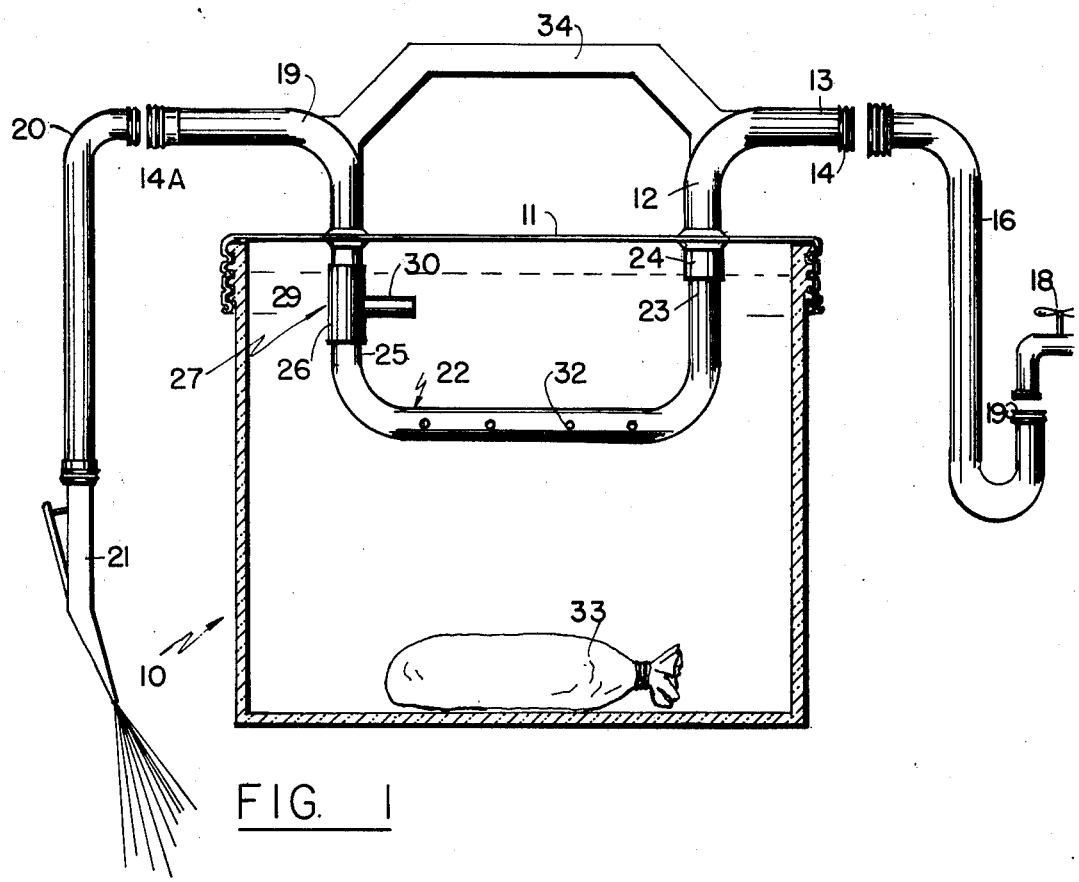
FIG. 1 is a side elevation of the dispenser sectioned in part for clarity.
Figure 2:
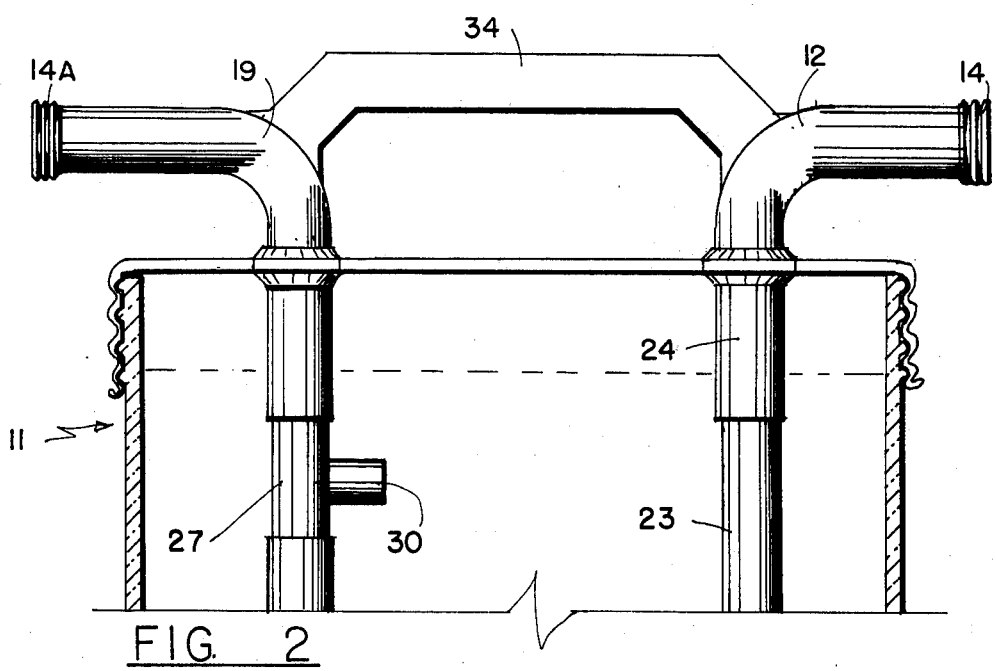
FIG. 2 is an enlarged vertical section through the detachable cover of the container.

Proceeding therefore to describe the invention in detail, reference character 10 illustrates generally a substantially cylindrical container manufactured from plastic or glass and having an open upper end normally closed by a screw threaded cover or cap 11 engaging screw threads at the upper end of the container.

A water inlet tube 12 extends through the cover 11 and is soldered thereto with the outer end 13 being provided with a screw threaded connection 14 adapted to be engaged with one end 15 of a flexible water hose 16. The other end 17 of the hose may be connected to a water tap 18 or similar source of water under pressure.

It is desirable that the connection 14 be of the loose ring type thus enabling same to be screwed to the connector 15 and to make a sealed joint therebetween.

A water outlet connector or union 19 also extends through the cover or cap 11 and is soldered thereto and is provided with a similar connector 14A on the outer end thereof thus enabling a length of hose 20 to be detachably secured thereto in a manner similar to that hereinbefore described.

A conventional spray gun nozzle 21 may be connected to the other end of the hose 20 for controlling the flow of the water through the device.

Alternatively, of course, the dispenser may be connected in series in a water line feeding the flush tank or a urinal or toilet under which circumstances, solid tubing would be used.

A U-shaped tubular connector collectively designated 22 is provided within the container, one end 23 of which is secured to the lower end 24 of the inlet connector 12, either by solder or by other conventional means.

The other leg 25 of this U-shaped connector is secured to one side 26 of a T shaped fitting collectively designated 27 with the other leg 28 of the T shaped fitting being secured to the lower end 29 of the outlet connector 19. Once again this connection may be means of soldering or other conventional means.

The offstanding leg 30 of the T shaped fitting 27 extends substantially at right angles to the legs 26 and 28 and communicates with the interior of the container as clearly shown.

The fitting of the U-shaped connector 22 is such that this U-shaped connector depends downwardly into the container and terminates spaced from the base 31 thereof as clearly illustrated and this U-shaped connector is provided with one or more relatively small apertures 32 in the wall thereof.

A powdered or solid chemical (not illustrated) is contained within a porous sac or bag 33 and is adapted to be dissolved by water within the container and this sac or bag normally rests upon the base 31 below the U-shaped connector 22 and, more importantly, below the T fitting leg 30.

An arcuately curved handle 34 extends between the inlet and outlet connectors 12 and 19 exteriorally of the cap or cover 11 to enable the operator to support the container when in use, if same is not permanently installed in series with a water line.

In operation, the desired chemical either a bactericide, fungicide, or the like is placed within the bag or sac 33 and this in turn is placed within the container whereupon the screw cap is secured to the upper end thereof.

The water hose 16 is secured to the inlet union 12 and the water hose 20 is secured to the water outlet 19 whereupon cap 18 is turned on so that water under pressure flows through hose 16, through the inlet union 12, through the U-shaped connector 22, to the outlet union 19 and thence to hose 20 where the use of the water may be controlled by the spray gun or nozzle 21 held by the operator.

As the water passes through the U-shaped connector, a small percentage thereof exits through the apertures 32 and gradually fills the container expelling air through the T fitting 27.

As soon as the T fitting is covered, there is of course, a relatively small quantity of air compressed between the upper surface of the water and the cap or lid 11, until the pressure thereof equals the water pressure from tap 18.

The water in the container gradually dissolves the chemical in the bag 33 and the water in the container is expelled through the leg 30 of the T fitting 27 and back into the main water stream due to the slight suction created at the T fitting by the passage of water thereby. This means that a controlled amount of water is removed from the container which, of course, is replaced by water entering same through the apertures 32.

When the spraying is completed, the tap 18 is shut off and if the spray gun or nozzle is removed or remains open, there will, under many circumstances, be a siphoning action which will remove the water from the container until the level of the water in the container falls below the T branch 30 which, of course, will break the vacuum and prevent further water from being removed. This means that there is always a quantity of water remaining in the container which gradually dissolves chemical in bag 33 so that when the device is next used, a supply of treated water is available. Furthermore, it prevents the chemical from drying out and deteriorating when the device is not being used.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. A chemical dispenser adapted to be connected with a source of water under pressure and to be used in conjunction with a powdered water soluble chemical in said dispenser; comprising in combination a container, a detachable cover for said container, water inlet and water outlet means connected to said detachable cover, said water inlet means being connectable to said source of water under pressure, an apertured tubular connector below said detachable cover and within said container when said detachable cover is attached to said container, connecting said water inlet means with said water outlet means, said tubular connector being substantially U-shaped and including a main portion lying substantially parallel to said detachable cover and spaced above the base of said container and being provided with a plurality of relatively small holes through the wall of said main portion, a water outlet branch connected to said water outlet means below said detachable cover and in said container when said detachable cover is attached to said container, said water outlet branch taking the form of a T pipe tubular member connected between said tubular connector and said water outlet means with one leg of said member communicating with the interior of said container above said main portion of said tubular connector and a handle extending between said water inlet and water outlet means exteriorally of said cover.

2. The dispenser according to claim 1 in which said water soluble chemical is contained in a porous bag situated in the base of said container and below said water outlet branch.

* * * * *